(12) United States Patent
Andrews

(10) Patent No.: US 8,617,086 B2
(45) Date of Patent: Dec. 31, 2013

(54) METHODS AND APPARATUSES FOR FULL-THICKNESS HOLLOW ORGAN BIOPSY

(75) Inventor: Christopher Andrews, Calgary (CA)

(73) Assignee: UTI Limited Partnership, Calgary, CA (US)

(*) Notice: Subject to any disclaimer, the term of this patent is extended or adjusted under 35 U.S.C. 154(b) by 0 days.

(21) Appl. No.: 13/174,267

(22) Filed: Jun. 30, 2011

(65) Prior Publication Data

US 2012/0004573 A1   Jan. 5, 2012

Related U.S. Application Data

(60) Provisional application No. 61/360,639, filed on Jul. 1, 2010.

(51) Int. Cl.
*A61B 10/00* (2006.01)
(52) U.S. Cl.
USPC ............ 600/567; 600/411; 600/562; 600/564
(58) Field of Classification Search
USPC .......................................... 600/411, 562–568
See application file for complete search history.

(56) References Cited

U.S. PATENT DOCUMENTS

| | | | | |
|---|---|---|---|---|
| 3,800,783 A * | 4/1974 | Jamshidi | ........................ | 600/567 |
| 4,776,346 A * | 10/1988 | Beraha et al. | ................. | 600/567 |
| 5,012,818 A * | 5/1991 | Joishy | ........................... | 600/567 |
| 6,582,395 B1 | 6/2003 | Burkett et al. | ............. | 604/96.01 |
| 7,778,682 B2 * | 8/2010 | Kumar et al. | ................. | 600/411 |
| 2006/0258953 A1 * | 11/2006 | Lee | .............................. | 600/562 |

FOREIGN PATENT DOCUMENTS

WO    WO 02/19890    3/2002

OTHER PUBLICATIONS

"A percutaneous endoscopically-assisted transenteric (PEATE) approach to full-thickness gastric biopsy," University Technologies International, 2010.
Andrews et al., "Percutaneous endoscopically assisted transenteric full-thickness gastric biopsy: initial experience in humans," *Gastrointest. Endosc.*, 73(5):949-54, 2011.

(Continued)

*Primary Examiner* — Sean Dougherty
(74) *Attorney, Agent, or Firm* — Fulbright & Jaworski LLP

(57) ABSTRACT

A method for obtaining a full thickness biopsy of the wall of a hollow organ, comprising obtaining an apparatus comprising a cannula comprising a proximal cannula end comprising a cutting edge; and a distal cannula end comprising a biased spring, the biased spring being coupled to a needle carrier and a releasable lock; and a needle disposed within the cannula and carried on the needle carrier, the needle comprising: a tip; a flange; a notch portion comprising a notch thickness; and a shaft comprising a shaft thickness; where the shaft thickness is greater than the notch thickness and the releasable lock is configured to hold the cannula in a withdrawn position relative to the needle; obtaining a patient having skin, a first wall, and a second wall; creating an incision through the skin of the patient; inserting the apparatus into the incision; advancing the apparatus through the first wall and the second wall; withdrawing the cannula relative to the needle; locking the cannula with the releasable lock; aligning the notch portion such that the notch portion straddles the second wall; releasing the releasable lock such that the cutting edge of the cannula passes completely through the second wall creating a full-thickness biopsy; and withdrawing the apparatus from the patient.

2 Claims, 3 Drawing Sheets

(56) References Cited

OTHER PUBLICATIONS

Forster et al., "Absence of the interstitial cells of Cajal in patients with gastroparesis and correlation with clinical findings," *J. Gastrointes. Surg.*, 9(1): 102-108, 2005.

Fraser et al., "A novel method of full thickness gastric biopsy by a percutaneous endoscopic transenteric (PETE) approach," abstract 4, *Abstracts of the 3rd International Meeting of Neurogastroenterology and Motility*, Aug. 2009.

Fraser et al., "A novel method of full-thickness gastric biopsy via a percutaneous, endoscopically assisted, transenteric approach," *Gastrointestinal Endoscopy*, 71(4):831-834, 2010.

Iwasaki et al., "A deficiency of gastric interstitial cells of Cajal accompanied by decreased expression of neuronal nitric oxide synthase and substance P In patients with type 2 diabetes mellitus," *J. Gastroenterol.*, 41(11): 1076-1087, 2006.

Miller et al., "Distribution of interstitial cells of Cajal and nitrergic neurons in normal and diabetic human appendix," *Neurogastroenterol., Motil.*, 40(4):349-357, 2008.

Ordög el al., "Remodeling of networks of interstitial cells of Cajal in a murine model of diabetic gastroparesis," *Diabetes*, 49(10):1731-1739, 2000.

Rajan et al., "Endoscopic 'no hole' full-thickness biopsy of the stomach to detect myenteric ganglia," *Gastointestinal Endoscopy*, 68(2): 301-307, 2008.

Rajan et al., "Evaluation of endoscopic approaches for deep gastric-muscle-wall biopsies: what works?" *Gastrointest. Endosc.*, 67(2):297-303, 2008.

\* cited by examiner

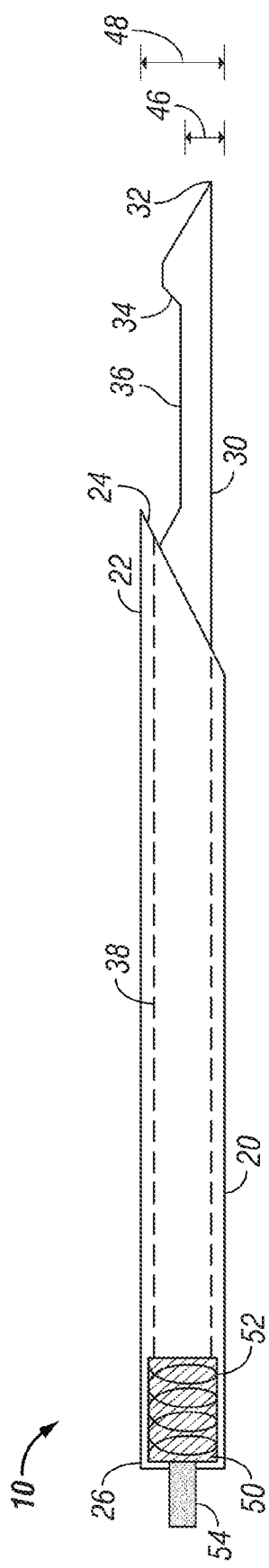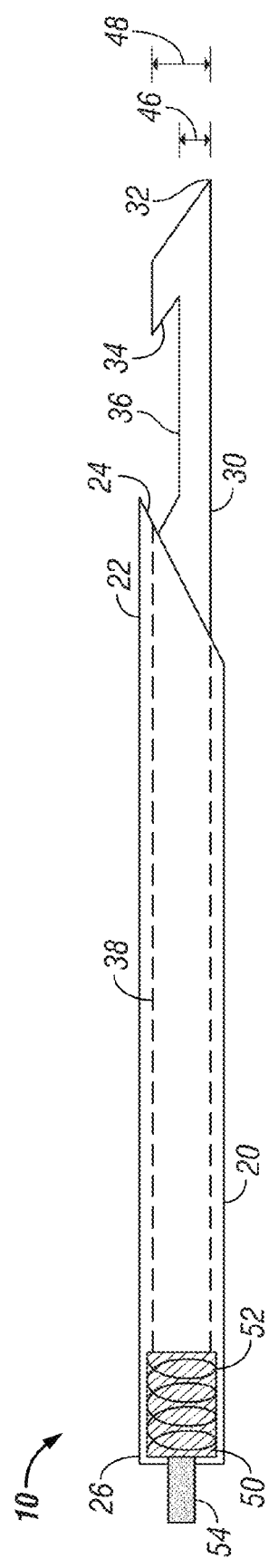

METHODS AND APPARATUSES FOR FULL-THICKNESS HOLLOW ORGAN BIOPSY

CROSS-REFERENCE(S) TO RELATED APPLICATION(S)

This application claims priority to U.S. Provisional Patent Application Ser. No. 61/360,639 filed Jul. 1, 2010. This provisional application is expressly incorporated by reference.

FIELD OF THE INVENTION

This invention relates generally to field tissue sample collection. Specifically, methods and apparatuses for taking tissue samples from hollow organs are disclosed.

BACKGROUND

Current designs for biopsy guns for soft tissue applications use a cutting cannula to collect the tissue sample. The most commonly used method has the cannula sliding over a stable or retracting inner needle which contains a notch for collection of the tissue. The cannula is a hollow cylinder with a sharp leading edge. These designs are oriented toward solid soft tissues (e.g., liver, prostate) and tumors that arise from them.

Current methods and devices for obtaining soft tissue samples from hollow organs (e.g., stomach, intestines) require laparoscopy or laparotomy. These methods and devices often fail to collect the portions of interest in the target organ. In addition, these methods and devices have a high perforation rate, leading to patient injury and increased healing time. The following are incorporated by reference:

"Percutaneous endoscopically assisted transenteric full-thickness gastric biopsy: initial experience in humans." Andrews C N, Mintchev P, Neshev E, Fraser H F, Storr M, Bathe O F, Urbanski S J. Gastrointest Endosc. 2011 May; 73(5):949-54. Epub 2011 Mar. 9.

"The London Classification of gastrointestinal neuromuscular pathology: report on behalf of the Gastro 2009 International Working Group." Knowles C H, De Giorgio R, Kapur R P, Bruder E, Farrugia G, Geboes K, Lindberg G, Martin J E, Meier-Ruge W A, Milla P J, Smith V V, Vandervinden J M, Veress B, Wedel T. Gut. 2010 July; 59(7):882-7

"Absence of the interstitial cells of Cajal in patients with gastroparesis and correlation with clinical findings," J Gastrointest Surg, 2005; 9(1):102-8, Forster J, Damjanov I, Lin Z, Sarosiek I, Wetzel P, McCallum R W.

"A deficiency of gastric interstitial cells of Cajal accompanied by decreased expression of neuronal nitric oxide synthase and substance P in patients with type 2 diabetes mellitus," J Gastroenterol, 2006; 41(11):1076-87, Iwasaki H, Kajimura M, Osawa S, Kanaoka S, Furuta T, Ikuma M, Hishida A.

"Distribution of interstitial cells of Cajal and nitrergic neurons in normal and diabetic human appendix," Neurogastroenterol Motil, 2008; 20(4):349-57, Miller S M, Narasimhan R A, Schmalz P F, Soffer E E, Walsh R M, Krishnamurthi V, Pasricha P J, Szurszewski J H, Farrugia G.

"Remodeling of networks of interstitial cells of Cajal in a murine model of diabetic gastroparesis," Diabetes, 2000; 49(10):1731-9, Ordog T, Takayama I, Cheung W K, Ward S M, Sanders K M.

"Diabetic gastroparesis," N Engl J Med, 2007; 356(8):820-9, Camilleri M.

"Evaluation of endoscopic approaches for deep gastric-muscle-wall biopsies: what works?" Gastrointest Endosc, 2008; 67:297-303, Rajan E, Gostout C J, Lurken M S, et al.

"Endoscopic 'no hole' full-thickness biopsy of the stomach to detect myenteric ganglia," Gastrointest Endosc, 2008; 68:301-7, Rajan E, Gostout C J, Lurken M S, et al.

SUMMARY

One embodiment of the invention comprises a biopsy collection apparatus comprising a cannula comprising a proximal cannula end comprising a cutting edge, and a distal cannula end comprising a biased spring, the biased spring being coupled to a needle carrier and a releasable lock; and a needle disposed within the cannula and carried on the needle carrier, the needle comprising: a tip, a flange, a notch portion comprising a notch thickness, and a shaft comprising a shaft thickness, where the shaft thickness is greater than the notch thickness and the releasable lock is configured to hold the cannula in a withdrawn position relative to the needle.

In certain embodiments, the flange is angled away from the tip. In other embodiments, the flange is angled toward the tip. In still further embodiments, the notch portion further comprises graduated markings.

Another embodiment comprises a biopsy collection apparatus comprising a cannula comprising a proximal cannula end comprising a cutting edge and a distal cannula end comprising a biased spring coupled to a needle carrier and a releasable lock; and a needle disposed within the cannula and carried on the needle carrier, the needle comprising: a guide portion having a guide thickness, a tapered portion, and a shaft portion having a shaft thickness, where the shaft thickness is greater than the guide thickness and the releasable lock is configured to hold the cannula in a withdrawn position relative to the needle.

Some embodiments comprise a method for obtaining a full thickness biopsy of the wall of a hollow organ, comprising obtaining an apparatus comprising a cannula comprising a proximal cannula end comprising a cutting edge; and a distal cannula end comprising a biased spring, the biased spring being coupled to a needle carrier and a releasable lock; and a needle disposed within the cannula and carried on the needle carrier, the needle comprising: a tip; a flange; a notch portion comprising a notch thickness; and a shaft comprising a shaft thickness; where the shaft thickness is greater than the notch thickness and the releasable lock is configured to hold the cannula in a withdrawn position relative to the needle; obtaining a patient having skin, a first wall, and a second wall; creating an incision through the skin of the patient; inserting the apparatus into the incision; advancing the apparatus through the first wall and the second wall; withdrawing the cannula relative to the needle; locking the cannula with the releasable lock; aligning the notch portion such that the notch portion straddles the second wall; releasing the releasable lock such that the cutting edge of the cannula passes completely through the second wall creating a full-thickness biopsy; and withdrawing the apparatus from the patient.

Other embodiments comprise a method for obtaining a full thickness biopsy of the wall of a hollow organ, comprising: obtaining an apparatus comprising: a cannula comprising: a proximal cannula end comprising a cutting edge; and a distal cannula end comprising a biased spring coupled to a needle carrier and a releasable lock; and a needle disposed within the cannula and carried on the needle carrier, the needle comprising: a needle tip; a guide portion having a guide thickness; a tapered portion; and a shaft portion having a shaft thickness; where the shaft thickness is greater than the guide thickness and the releasable lock is configured to hold the cannula in a withdrawn position relative to the needle; obtaining a patient having skin, a first wall, and a second wall; creating an incision through the skin of the patient; inserting the apparatus into the incision; advancing the apparatus through the first wall; withdrawing the cannula relative to the needle; locking the cannula with the releasable lock; tenting the second wall with the needle tip; releasing the releasable lock such that the cutting edge of the cannula passes completely through the second wall creating a full-thickness biopsy; and withdrawing the apparatus from the patient.

BRIEF DESCRIPTION OF THE DRAWINGS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a connector that "comprises," "has," "includes" or "contains" one or more elements possesses those one or more elements, but is not limited to possessing only those elements. For example, in a needle comprising a tip and a notch portion, the needle includes the specified elements but is not limited to having only those elements. For example such a needle could also comprise graduated markings.

The term "patient" may include any human patient or any animal patient with hollow organs.

Further, a device or structure that is configured in a certain way is configured in at least that way, but it can also be configured in other ways than those specifically described.

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention.

FIG. 1 illustrates an embodiment of the biopsy collection apparatus.

FIG. 2 illustrates an embodiment of the biopsy collection apparatus.

FIGS. 3A-3D illustrate an embodiment of the biopsy collection apparatus in use in the stomach of a patient.

Figure 4:
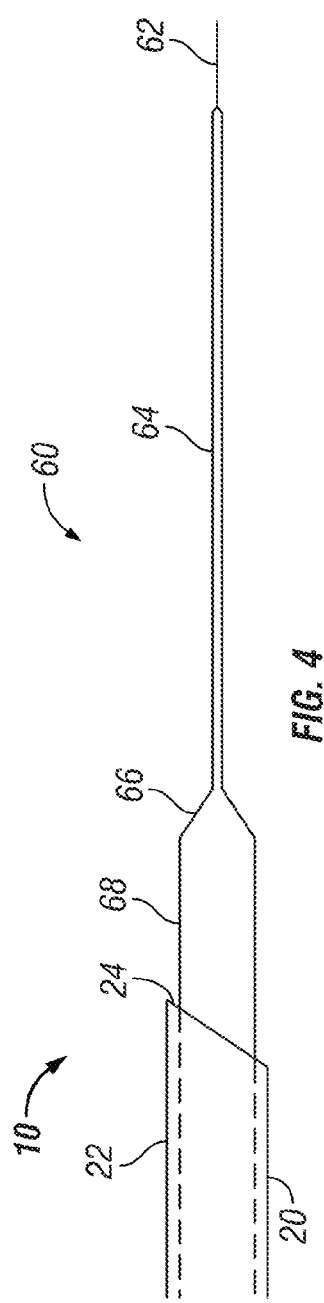

FIG. 4 illustrates an embodiment of the biopsy collection apparatus.

Figure 5:
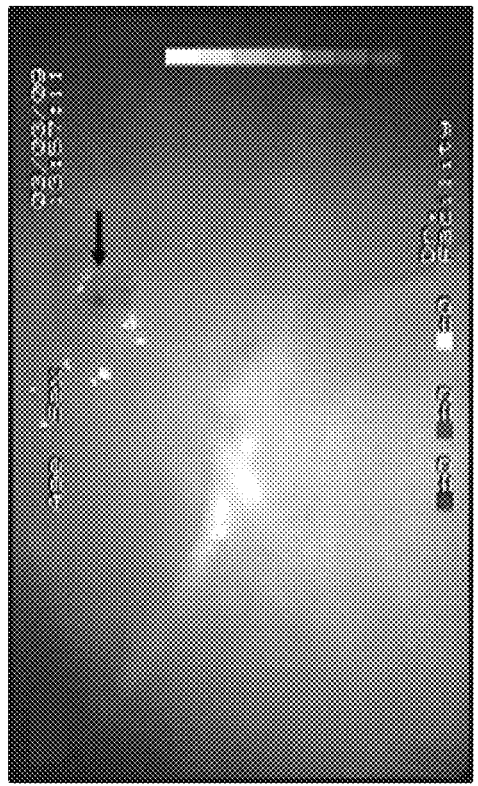

FIG. 5 illustrates an endoscopic view of the mucosal defect immediately after the biopsy specimen is taken and the biopsy collection apparatus is withdrawn.

Figure 6:

FIG. 6 illustrates a small locus of a scar seen on the parietal peritoneum at necropsy.

DETAILED DESCRIPTION OF EXEMPLARY EMBODIMENTS

Exemplary embodiments of the present disclosure are directed to methods and apparatuses for obtaining a full-thickness biopsy in a hollow organ. Current methods and devices for obtaining soft-tissue samples do not allow a user (e.g. a surgeon) to access all portions of a hollow organ.

For example, in some instances a surgeon may desire access to the enteric nervous system of the stomach. Because the enteric nervous system lies within the myenteric plexus between the muscle layers of the stomach, it is not accessible by standard biopsy forceps. Thus, tissue must be obtained by laparoscopy or laparotomy, procedures that are more invasive than a biopsy. In addition to being more invasive than biopsies, laparoscopic and laparotomic procedures are also more likely to puncture the stomach wall, leading to increased incidents of injury and potentially extending patient recovery time.

Turning now to the figures, FIG. 1 illustrates one embodiment of a biopsy collection apparatus 10 with the cannula in the cocked position. Apparatus 10 comprises a cannula 20 which surrounds an inner needle 30. Needle 30 and cannula 20 are configured to move relative to one another for the collection of a tissue sample.

Cannula 20 is hollow and substantially cylindrical in shape, and comprises a proximal end 22 and a distal end 26. Proximal end 22 is configured to be inserted into an incision made in the skin of a patient (not shown). Proximal end 22 comprises a cutting edge 24 that is configured to cut through the tissue of a target organ. In some embodiments, cannula may be a 14-gauge or a 12-gauge cannula.

In the illustrated embodiment, cannula 20 comprises a needle carrier 50, a biased spring 52, and a releasable lock 54, all located at distal end 26. Shaft 38 of needle 30 is coupled to needle carrier 50. Releasable lock 54 is configured to hold biased spring 52 in a cocked position. Biased spring 52 may comprise any suitable elastic material, including but not limited to alloyed metals or elastic polymers. When apparatus 10 is cocked, needle 30 is advanced from cannula 20 and cannula 20 is withdrawn relative to needle 30. Releasable lock 54 may be engaged to release cannula 20, placing apparatus 20 in an uncocked position. When apparatus 10 is in an uncocked position, notch portion 36 of needle 30 is withdrawn into cannula 20, and cannula 20 is advanced relative to needle 30.

Needle 30 is disposed within cannula 20 such that each moves relative to the other. Needle 30 comprises a tip 32 configured to puncture tissue walls (e.g., a patient's abdominal wall or stomach wall). Needle 30 comprises a notch portion 36 comprising a notch thickness 46 and a shaft portion 38 comprising a shaft thickness 48, with shaft thickness 48 being greater than notch thickness 46. Notch portion 36 is defined on one end by a flange 34. In the embodiment shown, flange 34 is angled toward tip 32 of needle 30, forming an obtuse angle between flange 34 and notch portion 36. As shown in the illustrated embodiment, flange 34 may be contoured to allow for repositioning of needle 30 after apparatus 10 is cocked but before cannula 20 is fired.

Turning now to FIG. 2, an alternative embodiment of apparatus 10 is shown. In most respects, the embodiment depicted in FIG. 2 is equivalent to the embodiment depicted in FIG. 1.

One difference in the embodiment shown in FIG. 2 is the angle of flange 34: in the embodiment shown in FIG. 2, flange 34 is angled away from tip 32 of needle 30, such that an acute angle is formed between flange 34 and notch portion 36. This is so because in some applications, the target tissue may slide off notch portion 36 when cannula 20 is fired. In embodiments where flange 34 faces rearward, the target tissue is more likely to stay in place. In some embodiments, flange 34 may comprise a sharp edge. In still other embodiments, flange 34 may be such that a right angle is formed between flange 34 and notch portion 36.

In certain embodiments, other mechanisms may be used to store potential energy instead of biased spring 52 and releasable lock 54. For example, a shape memory alloy configured to rapidly advance cannula 20 toward tip 32 of needle 30 may be used. Or pneumatic or electro-mechanical actuators may be used to withdraw and advance cannula 20 relative to tip 32 of needle 30.

Still other embodiments may omit releasable lock 54. In such embodiments, an operator (such as a surgeon) may withdraw cannula 20 relative to needle 30, hold it in place by hand, then release cannula 20.

Figure 3A:
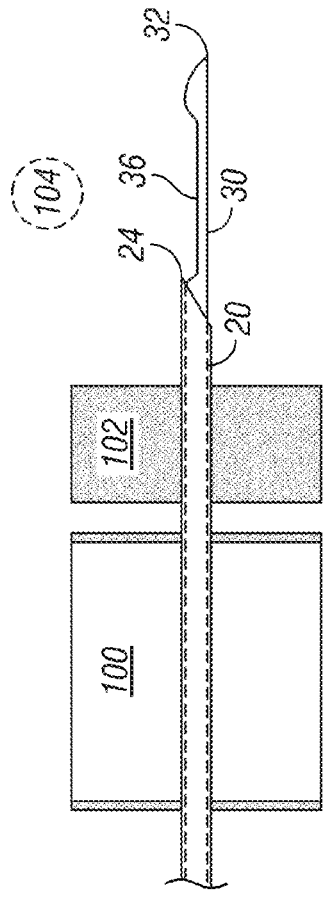

Turning now to FIGS. 3A-3D, a step-by-step process of using the apparatus is shown. First, an incision is made in the skin of a patient (not shown). As shown in FIG. 3A, apparatus 10, in the uncocked position, is inserted into the incision and through a first wall 100 and a second wall 102. In the embodiments discussed below, first wall 100 is the abdominal wall, while second wall 102 is the stomach. For ease of understanding, and in no way limiting the uses of the disclosed embodiments, the remainder of the discussion will refer to abdominal wall 100 and stomach wall 102. The disclosed invention may be used on other hollow organs such as the intestines, for example.

Figure 3B:
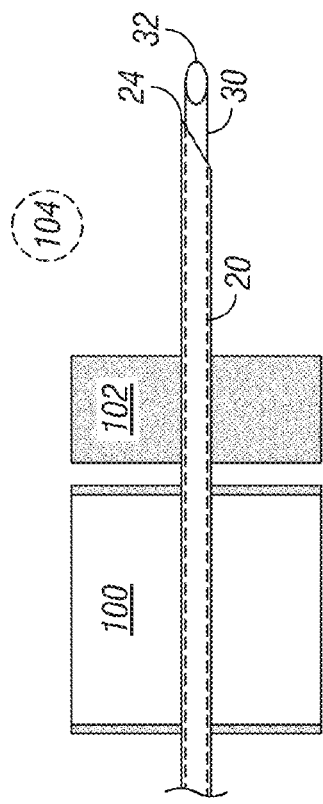

Tip 32 of needle 30 punctures abdominal wall 100 and stomach wall 102, allowing both cannula 20 and needle 30 to be inserted into the stomach cavity 104. As shown in FIG. 3B, once apparatus 10 has been inserted into stomach cavity 104, apparatus 10 is placed in the cocked position. When the apparatus is in the cocked position, needle 30 is advanced from cannula 20, and cannula 20 is withdrawn with respect to needle 30. Releasable lock 54 engages biased spring 52, needle carrier 50, or both to maintain apparatus 10 in cocked position until releasable lock 54 is triggered.

Figure 3C:
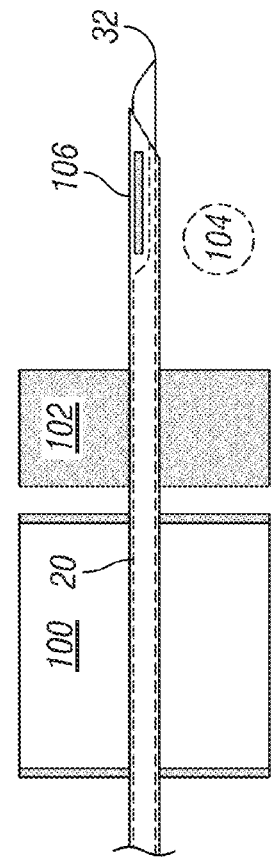
Figure 3D:
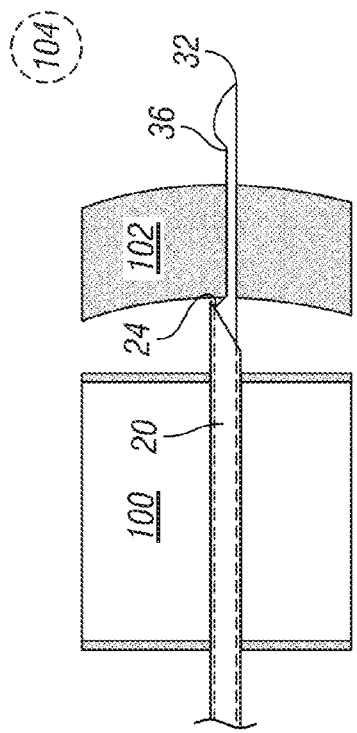

As shown in FIG. 3C, after apparatus 10 is placed in the cocked position, cannula 20 is withdrawn from stomach cavity 104 such that notch portion 36 of needle 30 straddles stomach wall 102 and cutting edge 24 of cannula 20 is outside stomach wall 102. As shown in FIG. 3D, once apparatus 10 is properly positioned, releasable lock 54 is triggered. Biased spring 54 propels cutting edge 24 of cannula 20 through stomach wall 102, toward tip 32 of needle 30. As cannula 20 passes through stomach wall 102 and advances past notch portion 36, a full-thickness biopsy 106 is removed from stomach wall 102.

Apparatus 10 is now in an uncocked position, and biopsy 106 is enclosed in cannula 20 between notch portion 36 and the inner wall of cannula 20. Apparatus 10 may be removed from stomach cavity 104. In some embodiments, biopsy 106 may be collected by cocking apparatus 10, removing biopsy 106 from notch portion 36, and returning apparatus 10 to the uncocked position.

Although FIGS. 3A-3D illustrate apparatus 10 in use in minimally-invasive biopsy context, the apparatus may be used during open surgery as well. In open surgery, the hollow organ may be directly exposed to the surgeon, such that the apparatus may not need to be inserted through an incision and abdominal wall 100. In such applications, an operator may place apparatus 10 in the uncocked position such that cannula 20 is advanced relative to needle 30. Tip 32 of needle 30 punctures stomach wall 102, allowing both cannula 20 and needle 30 to be inserted into the stomach cavity 104. Apparatus 10 may then be cocked and positioned as discussed above, such that notch portion 36 of needle 30 straddle stomach wall 102 and cutting edge of cannula 20 is outside stomach wall 102. Releasable lock 54 may then be triggered such that biased spring 54 propels cutting edge 24 of cannula 20 through stomach wall 102 toward tip 32 of needle 30. Similar to the procedure described above, as cannula 20 passes through stomach wall 102 and advances past notch portion 36, a full-thickness biopsy 106 is removed from stomach wall 102.

FIG. 4 illustrates another alternative embodiment of apparatus 10, which operates in a similar fashion to the apparatus illustrated in FIGS. 1 and 2 above except that a different needle is used. In the illustrated embodiment, apparatus 10 comprises tracking needle 60. Tracking needle 60 comprises a tip 62, a guide portion 64, a tapered portion 66, and a shaft portion 68.

The embodiment of FIG. 4 is used in a similar fashion as the embodiments discussed above. However, unlike the embodiments shown in FIGS. 3A-3B, in the embodiment in FIG. 4, tracking needle 60 is inserted into the incision in a cocked position. Tip 62 pierces abdominal wall 100 allowing guide portion 64 to pass through abdominal wall 100. Tip 62 is inserted into stomach wall 102, or "tents" it, but tip 62 does not pass through stomach wall 102. In certain embodiments, tip 102 may comprise a bulb, balloon, or umbrella configured to tent stomach wall 102. Once tip 62 abuts stomach wall 102, releasable lock 54 may be triggered. Cutting edge 24 of cannula 20 is projected past tip 62 and through stomach wall 102, collecting biopsy 106 within cannula 20. Apparatus 10 may then be withdrawn from the patient with biopsy 106 within cannula 20. In some embodiments, biopsy 106 may be removed from apparatus 10 by placing apparatus 10 in a cocked position, removing biopsy 106 from around guide portion 64.

Two practical applications of the disclosed invention will now be discussed.

Example I

Animal Trial

Gastroparesis is a motility disorder of the stomach characterized by symptoms of delayed gastric emptying. These symptoms may include nausea, vomiting, bloating, and abdominal pain. Diagnosis is made by typical clinical history and confirmation with a gastric emptying test after exclusion of structural abnormalities or malignancy.

The pathophysiology of gastroparesis is complex. Recent evidence has shown histopathologic disruption of the enteric nervous system (ENS) in full-thickness stomach specimens of patients with gastroparesis. Altered mediators of oxidative stress have also been found in animal models of gastroparesis. Because the myenteric plexus (which contains the majority of ENS neurons and interstitial cells of Cajal) is sandwiched between the circular and longitudinal muscles of the stomach, it is not accessible with standard mucosal biopsy forceps. Obtaining gastric ENS tissue, to date, has typically required a laparoscopy or laparotomy. Experimental endoscopic approaches have either failed to access ENS tissue or had a high perforation rate.

Methods

This protocol was approved by the University of Calgary Animal Care Committee. Three healthy, mongrel dogs (2 female, average weight 17.6 kg) were fasted overnight. One prophylactic dose of antibiotic (enrofloxacin, 5 mg/kg intravenously; Bayer, Montreal, QC) was administered before the procedure. General anesthesia was induced with thiopental sodium, 20 mg/kg intravenously (Vetoquinol; Lavaltrie, QC) and maintained with 1% to 3% isoflurane inhaled (Halocarbon Laboratories, River Edge, N.J.).

The Percutaneous Endoscopically Assisted Transenteric Technique

Each dog underwent upper endoscopy, and a suitable biopsy area was chosen, based on indentation of the ventral antral wall by external finger pressure on the abdomen and by transillumination with the endoscope. By using a sterile technique, local anesthesia was administered (lidocaine 1%; AstraZeneca, Montreal, QC) in the skin and along the tract to the stomach. Confirmation of a direct tract was made by visualizing the anesthetic needle penetrating the stomach. A 3-mm incision was made through the abdominal skin with a scalpel. The stomach was then fully distended with air.

A 14-gauge biopsy needle set (9-cm length, 20-mm throw; Quick-Core Biopsy Needle Set, Cook Medical Inc, Bloomington, Ind.) was used. This set contains an internal needle with a notch on the shaft for collecting tissue, surrounded by a spring-loaded, cutting, 14-gauge cannula. The set was passed, uncocked, into the stomach under direct visualization. The spring was then cocked, and the internal needle containing the biopsy notch was exposed. The needle set was withdrawn until the cannula left the stomach, and the notch appeared to straddle the stomach wall. This was confirmed by tenting of the gastric wall by the cannula pushing from the serosal side. The needle was then fired, taking a full-thickness gastric biopsy specimen.

The needle set was then withdrawn, and the biopsy tissue collected. The needle set was then passed again through the same abdominal incision and the procedure repeated three more times at adjacent regions of the antrum at least 10 mm apart. No mucosal or full-thickness closure interventions were planned or performed. Skin incisions were closed with tissue glue (methacrylate; Ted Pella, Redding, Calif.), and the dogs were recovered from anesthesia.

Follow-Up

All dogs received buprenorphine, 0.02 mg/kg (Schering-Plough, Montreal, QC), for pain control before, and ten hours after, the procedure. All dogs were monitored daily for symptoms of peritonitis, bleeding, or fever (rectal temperature and hemoglobin daily for the first two days postoperatively).

Dogs were followed for four weeks. Dogs then had repeat endoscopy (all dogs), and laparoscopy (1 dog) under general anesthesia as previously done and were then killed with sodium barbital, 2 mL/4.5 kg (Bimeda-MTC, Cambridge, ON), followed by necropsy. Biopsy material was immediately fixed in 10% formalin and later paraffin was embedded and sectioned. Material was stained for hematoxylin and eosin (for general assessment and muscle), c-kit (for interstitial cells of Cajal), PGP9.5 (for neuronal cells), and S-100 (for glial cells) by using standard methods.

Results

Each dog had four gastric biopsy specimens taken at the initial endoscopy. Although a small mucosal defect was often seen shortly after biopsy upon removal of the needle set, this spontaneously sealed within 10 seconds. FIG. 5 shows a photograph of this mucosal defect. Similarly, an insignificant amount of oozing blood was seen after biopsy, but this stopped spontaneously. No hematoma was seen at any of the biopsy sites.

All dogs survived the four-week follow-up period. No signs of peritonitis or pain were observed either immediately after the operation or during the following four weeks. During the first two postoperative days, all dogs were fed with canned (wet) dog food, and two of the dogs had looser stools during this period. After we switched them to a dry dog food, their stools normalized. All dogs maintained their initial weights.

In all dogs, at week four, the abdominal skin incision was barely discernable. Repeat endoscopy showed no perceptible scarring in two dogs, and a suggestion of mild mucosal deformity in the region of biopsy in one dog. The gastric mucosa was completely healed in all cases, with no evidence of inflammation, ulceration, or perforation. There was no evidence of adhesion formation between the abdominal wall and the stomach, and minimal scarring was seen on the parietal peritoneum of the abdominal wall, as shown in FIG. 6. No scarring could be perceived visually on the serosal aspect of any of the stomachs in the collapsed (ie, undistended) state, either at laparoscopy (one dog) or after en bloc resection with detailed inspection at necropsy (all dogs).

All biopsies except two of the first biopsies showed intact gastric wall with ENS elements. Full-thickness histology is shown in FIG. 4. Specific staining for interstitial cells of Cajal, neurons, and glia confirmed the presence of those tissue elements (not shown). Average fresh biopsy size was approximately 2 mm by 4 mm laid out on blotter paper.

Discussion

This study confirms the feasibility and safety of the novel percutaneous endoscopically assisted transenteric approach (PEATE) biopsy technique in a canine model. The technique is easily performed, similar in some aspects to insertion of a percutaneous gastrostomy feeding tube, a routine endoscopic procedure. PEATE gastric biopsy also reliably obtains ENS tissue and appears safe from animal data.

Potential risks of this procedure include peritonitis because of leakage of gastric content into the abdominal cavity after the biopsy specimen is taken. This likelihood is low because of the ability of the gastric muscle to contract and reduce the size of the defect; the function of the omentum to inhibit leakage; and mucosal clips that may be applied endoscopically if necessary. Although placing clips may be prudent in humans, the risk of peritonitis would be expected to be lower in humans because of the thicker stomach relative to the biopsy size. Peritonitis may also occur because of infection introduced by the percutaneous approach, but this is minimized by adhering to strict sterile technique for the procedure. The risk of bleeding is also minimized by the fact that this biopsy is not done blindly. If significant bleeding were to occur, it would be expected as soon as the needle set was passed into the stomach; thus, action could be taken before the cannula was fired to minimize damage. Bleeding that is not endoscopically visible (eg, into the peritoneal cavity) is typically minor, based on experience from percutaneous gastrostomy tube insertion. There are other risks of performing this procedure in humans with comorbidities (such as food retention, obesity, or immune deficiency), but these conditions would not be expected to pose an excessive risk.

Assessment of ENS histology or biomarkers appears promising in gastroparesis. This new technique may provide a valuable research tool in understanding gastric motility disorders in humans, which cause a huge morbidity burden. Furthermore, with the simplicity of this technique and the fact that it can be practiced by any endoscopist, routine assessment of ENS tissue easily could be adopted if shown to be of value in diagnosis.

Example II

Human Trial

This protocol was approved by University of Calgary Research Ethics Board, and all patients gave written informed consent. After an overnight fast, one prophylactic dose of antibiotic (cefazolin 2 g IV) was administered before the procedure. Conscious sedation with fentanyl and midazolam, or propofol was given as required.

PEATE Technique

Each patient underwent upper endoscopy and a suitable biopsy area was chosen based on indentation of the ventral antral wall by external finger pressure on the abdomen and by transillumination with the endoscope. Using sterile technique, local anesthesia (lidocaine 2%; Astrazeneca, Montreal, QC) was given in the skin and along the tract to the stomach. Confirmation of a direct tract was made by visualizing the anesthetic needle penetrating the stomach. A 3 mm incision was made through the abdominal skin with a scalpel. The stomach was then fully distended with air.

A 14 gauge (G) biopsy needle set (9 cm length, 20 mm throw; Quick-Core Biopsy Needle Set, Cook Medical Inc, Bloomington, Ind.) was used. This set contains an internal needle with a notch on the shaft to collect tissue surrounded by a spring-loaded cutting 14 G cannula. The set was passed, uncocked, into the stomach under direct visualization. The spring was then cocked and the internal needle containing the biopsy notch was exposed. The needle set was withdrawn until the cannula left the stomach and the notch appeared to straddle the stomach wall. This was confirmed by tenting of the gastric wall by the cannula pushing from the serosal side. The needle was then fired, taking a full-thickness gastric biopsy.

The needle set was then withdrawn and the biopsy tissue collected. The needle set was then passed again through the same abdominal incision and the procedure repeated 3 more times at adjacent regions of the antrum. No mucosal or full-thickness closure interventions were planned or performed. A sterile dressing (Op-Site) was placed over the skin incision for 24 hours. Patients were monitored for at least 3 hours post-operatively for signs of complications before being discharged.

I claim:

1. A method for obtaining a full thickness biopsy of the wall of a stomach of a patient, comprising:
    obtaining an apparatus comprising:
        a cannula comprising:
            a proximal cannula end comprising a cutting edge; and
            a distal cannula end comprising a biased spring, the biased spring being coupled to a needle carrier and a releasable lock; and
        a needle disposed within the cannula and carried on the needle carrier, the needle comprising:
            a tip;
            a flange;
            a notch portion comprising a notch thickness; and
            a shaft comprising a shaft thickness;
            where the shaft thickness is greater than the notch thickness and the releasable lock is configured to hold the cannula in a withdrawn position relative to the needle;
    creating an incision through the skin of the patient;
    inserting the apparatus into the incision;
    advancing the apparatus through the abdominal wall and the stomach wall of the patient;
    withdrawing the cannula relative to the needle;
    locking the cannula with the releasable lock;
    aligning the notch portion such that the notch portion straddles the stomach wall;
    releasing the releasable lock such that the cutting edge of the cannula passes completely through the stomach wall creating a full-thickness biopsy; and
    withdrawing the apparatus from the patient.

2. A method for obtaining a full thickness biopsy of the wall of a stomach of a patient comprising:
    obtaining an apparatus comprising:
        a cannula comprising:
            a proximal cannula end comprising a cutting edge; and
            a distal cannula end comprising a biased spring coupled to a needle carrier and a releasable lock; and
        a needle disposed within the cannula and carried on the needle carrier, the needle comprising:
            a needle tip;
            a guide portion having a guide thickness;
            a tapered portion; and
            a shaft portion having a shaft thickness;
            where the shaft thickness is greater than the guide thickness, the tapered portion is between and adjacent to the guide portion and the shaft portion, and the releasable lock is configured to hold the cannula in a withdrawn position relative to the needle;
    creating an incision through the skin of the patient;
    inserting the apparatus into the incision;
    advancing the apparatus through the abdominal wall of the patient;
    withdrawing the cannula relative to the needle;
    locking the cannula with the releasable lock;
    tenting the stomach wall with the needle tip;
    releasing the releasable lock such that the cutting edge of the cannula passes completely through the stomach wall creating a full-thickness biopsy; and
    withdrawing the apparatus from the patient.

* * * * *